United States Patent [19]

Kelly et al.

[11] Patent Number: 4,595,628
[45] Date of Patent: Jun. 17, 1986

[54] SOIL REPELLENT FLUORINATED ESTERS OF MULTI-RING ANHYDRIDE SYSTEMS

[75] Inventors: Michael G. Kelly, Coventry, R.I.; Willi R. Steckelberg, Hofheim, Fed. Rep. of Germany

[73] Assignee: American Hoescht Corporation, Somerville, N.J.

[21] Appl. No.: 635,764

[22] Filed: Jul. 30, 1984

Related U.S. Application Data

[63] Continuation of Ser. No. 355,800, Mar. 8, 1982, Pat. No. 4,472,466.

[51] Int. Cl.$^4$ .................. B05D 5/00; C07C 69/76; D06M 13/20
[52] U.S. Cl. ........................ 428/265; 8/115.64; 8/DIG. 4; 8/DIG. 21; 427/393.4; 428/267; 428/378; 428/395; 560/76; 560/89; 560/91
[58] Field of Search ....... 8/115.64, DIG. 4, DIG. 21; 427/393.4; 428/265, 267, 378, 395; 560/76, 89, 91

[56] References Cited

U.S. PATENT DOCUMENTS 4,063,024 12/1977 Sandler.

*Primary Examiner*—James C. Cannon
*Attorney, Agent, or Firm*—Hugh C. Crall; Stephan P. Williams

[57] ABSTRACT

Fluorinated esters based on multi-ring anhydride systems are disclosed which have excellent anti-soiling properties, durability and resistance to laundering. The compounds are represented by the formula

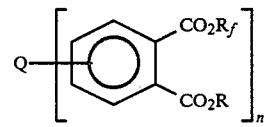

wherein n is 2 or 3, Q is a linking group such as —CO—, —O—, or $(C_aH_{2a+2-n})-(O_2C)_{\overline{n}}$, $R_f$ is a fluorinated radical, and R is derived from an epoxide such as ethylene oxide or epichlorohydrin. Also disclosed are polyester and nylon fibers having these compounds incorporated therein, and a process for producing such soil-repellent fibers.

16 Claims, No Drawings

SOIL REPELLENT FLUORINATED ESTERS OF MULTI-RING ANHYDRIDE SYSTEMS

CROSS-REFERENCES TO RELATED APPLICATIONS

This application is a continuation of U.S. patent application Ser. No. 355,800, filed Mar. 8, 1982, now U.S. Pat. 4,472,466.

BACKGROUND OF THE INVENTION

This invention relates to fluorinated compositions which impart oil and water repellency to synthetic fibers, particularly polyester and nylon fibers, and thus function as anti-soil agents. In particular, this invention relates to fluorinated esters of benzene anhydrides which are joined through a carbon-carbon bond or a linking group to form a multi-ring system.

DESCRIPTION OF THE PRIOR ART

Compounds containing fluorinated groups are broadly known for use as anti-soil agents for synthetic fibers. Fluorinated polyacrylics are disclosed in U.S. Pat. Nos. 3,171,861 and 3,547,861. These compositions are generally not suitable for application to fibers prior to manufacture of textile fabric or prior to the dyeing of such fabric. In U.S. Pat. No. 3,646,153 fluorinated compositions which are compatible with the fiber-forming polymer are disclosed but these tend to be removed from the fiber upon laundering.

Saturated perfluoroalkyl esters having anti-soiling properties are disclosed in U.S. Pat. No. 3,860,613. Example 5 of this patent illustrates a compound having the formula

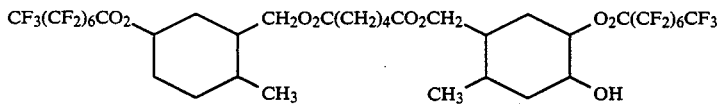

In U.S. Pat. No. 3,959,229 anti-soiling compositions are disclosed which are copolymers of (a) an aromatic dianhydride such as pyromellitic dianhydride or benzophenone tetracarboxylic dianhydride, (b) a fluorocarbon-diol, (c) a polyethylene glycol, and (d) a polyethylene terephthalate telomer.

U.S. Pat. No. 3,870,748 discloses anti-soiling compositions of the formula [R$_f$CH$_2$CH(OH)CH$_2$OOC]$_m$Q. At column 3, lines 23-25 is shown one possible Q, among a long list, having the formula

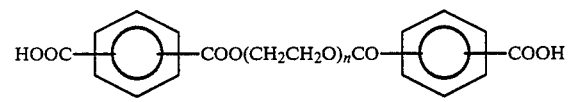

wherein n is 4 to 140, but no compounds based on this acid are disclosed. The compound having the formula

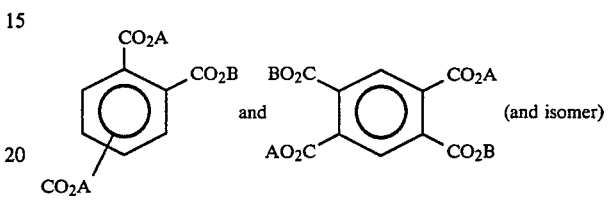

is typical of the compounds specifically disclosed.

Fluorinated soil repellent compositions which are said to be relatively durable and resistant to laundering or dry cleaning are disclosed in U.S. Pat. Nos. 4,209,610 and 4,219,625. The former patent discloses fluorinated esters of trimellitic and pyromellitic acids having the formulae

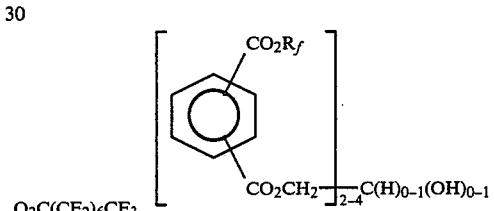

wherein typically A is —CH$_2$CH$_2$CF$_2$CF$_2$OCF(CF$_3$)$_2$ or —CH$_2$CH$_2$(CF$_2$)$_n$CF$_3$ (n=5-9) and B is —CH$_2$CH$_2$OH or —CH$_2$CH(OH)CH$_2$Cl. The latter patent discloses fluorinated polyol esters of phthalic and terephthalic acid. Typical of these are compounds of the formula $$\left[ \begin{array}{c} CO_2R_f \\ \phantom{X} \\ CO_2CH_2 \end{array} \right]_{2-4} \!\!\!\!C(H)_{0-1}(OH)_{0-1}$$

and particularly disclosed is the compound

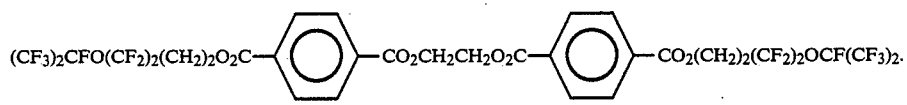

U.S. Pat. No. 4,063,024 discloses fluorinated trimellitic esters as soil repellents. One of the compounds said to be preferred has the formula

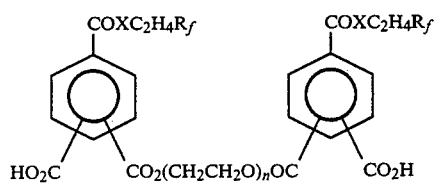

wherein X is O or S, n is 9 to 25, and R$_f$ is —(CF$_2$)$_Y$—CF(CF$_3$)$_2$ wherein Y is 2 to 8 (see col. 7). These compounds are said to have water absorption and wicking properties in contrast to other soil repellent compositions which repel water as well as oil.

SUMMARY OF THE INVENTION

Applicants have discovered a novel group of fluorinated esters based on multi-ring anhydride systems which have excellent anti-soiling properties, durability and resistance to laundering (wash-fastness) and dry cleaning when incorporated in polyester and nylon fibers. The compounds of the present invention may be depicted by the formula

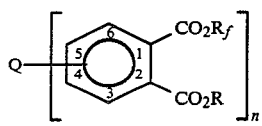
[I]

wherein
n is 2 or 3;

Q has a valence equal to n and is selected from the group consisting of a single carbon-carbon bond, $-C_mH_{2m}-$, $>C_mH_{2m-1}-$, $-CO-$, $-NH-$, $-O-$, $-S-$, $-SO_2-$, $(C_aH_{2a+2-n})(O_2C)_n$, $-CO(OCH_2CH_2)_bO_2C-$, $-CO_2C_6H_4O_2C-$, and $(CH_3)_2C(C_6H_4O_2C)_2$, wherein m is 1 to 6, a is 2 to 6, b is 2 to 10, and n is as defined above but cannot exceed a;

R is selected from $-CH_2CH(R_1)OH$, $-CH_2CH(R_1)OCH_2CH(R_1)OH$, $-CH_2CH(OH)CH_2X$, or $-CH_2CH(OH)CH_2OCH_2CH(OH)CH_2X$ wherein $R_1$ is hydrogen or methyl and X is chloro, bromo, hydroxy, or cyano; and $R_f$ is a fluorinated radical of the formula $-W(C_dF_{2d})Y$ wherein W has from 1 to 10 carbon atoms and is selected from alkylene and $W'-Z-(W'')_e$ where W' and W'' are alkylene, Z is O, S, NHCO, or NHSO$_2$, and e is 0 or 1, Y is hydrogen, fluoro, or perfluoroalkoxy of 1 to 6 carbon atoms, and d is 2 to 20. In the above formulation it is intended that the fluorinated radical $R_f$ may be straight, branched or cyclic in any of its alkylene or perfluoroalkylene chains.

The subject compounds have an excellent affinity for polyester and nylon fibers and may be incorporated with the raw or partially finished fiber by several methods. In one method the additive may be melt blended with the resin then extruded to form a fiber. In a second method the fiber may be treated with a solution, dispersion or emulsion of the additive in liquid medium, typically a solution in organic solvent or an aqueous emulsion. Either method is generally followed by subsequent heat treatment or annealing of the fiber.

The present compounds are sufficiently compatible with the resin that they become an integral part of the fiber, yet the incompatibility imparted by the fluorinated groups, and the mobility of the compounds, is sufficient to concentrate the compounds at the surface of the fiber, making the fiber hydrophobic and oleophobic. Once incorporated into the fiber surface, the present compounds resist being abraded or washed away because of their affinity for the resin and because of the low solubility of the compounds in aqueous soap solutions and dry cleaning solvents. The present compounds also allow satisfactory dyeing of the treated fiber, or may be applied together with a dyestuff from the same bath.

The present invention also includes polyester and nylon fibers, especially those derived from polyethylene terephthalate (PET) and nylon-6 and nylon-66, which have incorporated therewith at least one compound as defined above, and a process for producing such fibers which comprises contacting the fiber with a liquid emulsion, dispersion or solution containing at least one compound as defined above, and thereafter heat treating or annealing the fiber to impart oil and water repellency.

DESCRIPTION OF THE PREFERRED EMBODIMENTS

Preferred compounds within the composition defined by formula I described above may be categorized into two groups. In the first group of preferred compounds Q is selected from a single carbon-carbon bond, $-C_mH_{2m}-$, $-CO-$, $-NH-$, $-O-$, $-S-$, and $-SO_2-$. In the second group of preferred compounds, which can be generically referred to as polyol esters, Q is selected from $-CO_2(CH_2)_aO_2C-$, $-CO(OCH_2CH_2)_bO_2C-$, $-CO_2CH(CH_2O_2C)_2$, $CH_3C(CH_2O_2C)_3$, $CH_3CH_2C(CH_2O_2C)_3$, $C_4$, $-CO_2C_6H_4O_2C-$ and $(CH_3)_2C(C_6H_4O_2C)_2$. Within these preferred groups it is also preferred that Q is independently attached to the 4 or 5 position of each benzene ring with respect to the $-CO_2R_f$ moiety. These compounds are normally isolated as mixed isomers due to the non-specific reaction of the perfluorinated alcohol with the starting anhydride as explained below.

Particularly preferred compounds are those wherein W is alkylene of 2 to 6 carbon atoms, d is 2 to 12, and R is $-CH_2CH_2OH$, $-CH_2CH(OH)CH_2Cl$, $-CH_2CH(OH)CH_2OH$, or $-CH_2CH(OH)CH_2Br$ and those wherein $R_f$ is selected from $-CH_2CH_2(CF_2)_gCF_3$ or $-CH_2CH_2(CF_2)_hO$ $CF(CF_3)_2$ wherein g is 5 to 11 and h is 2 to 12. Most preferred are compounds of formula I wherein $R_f$ is $-CH_2CH_2(CF_2CF_2)_jCF_2CF_3$ and j is 2 to 5, and R is $-CH_2CH_2OH$ or $-CH_2CH(OH)CH_2Cl$.

Advantageous compounds of the present invention may be depicted by the following formulae wherein R and $R_f$ are as previously defined:

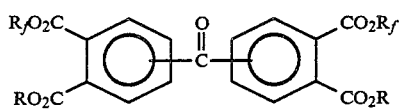

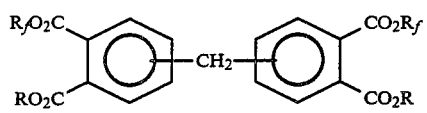

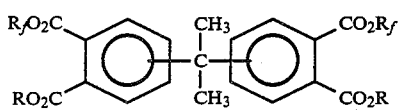

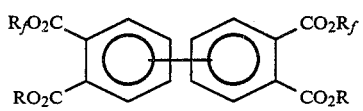

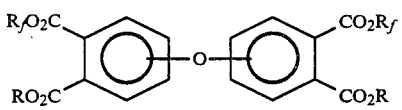

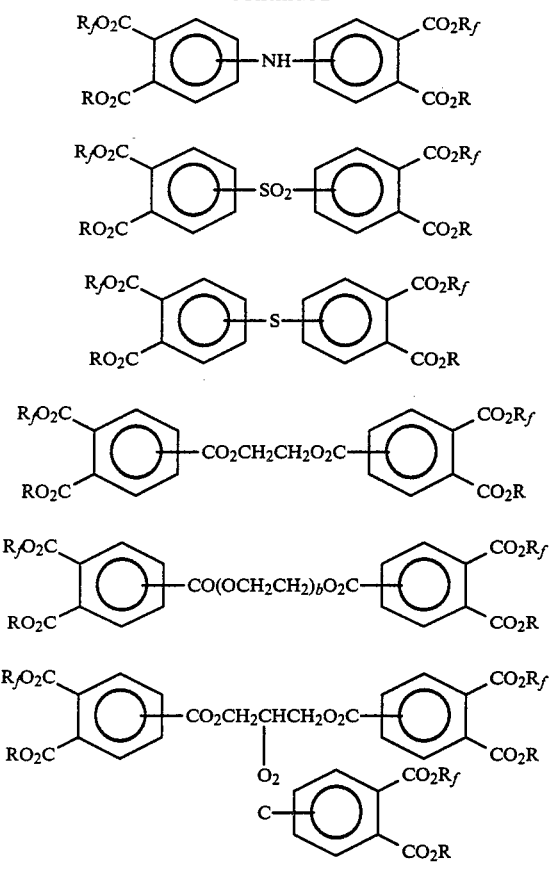

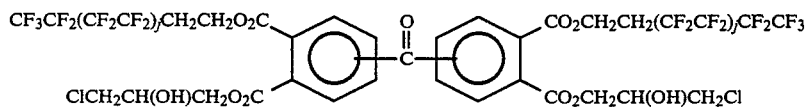

wherein j is 2 to 5.

The compounds of the present invention (formula I) may be prepared by reaction of the appropriate multi-ring anhydride with the selected fluorinated alcohol to form the corresponding carboxylic acid/half ester containing a fluorinated esterifying radical and a carboxy group. The free carboxy groups of this half ester are then esterified by base-catalyzed reaction with a suitable epoxide corresponding to the desired "R" group in the compound. This reaction scheme may be depicted as follows:

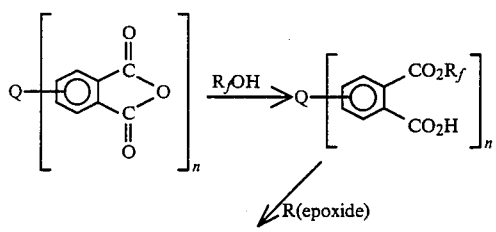

[I]

The above reaction scheme is well-known in the art, the particulars of which, as applied to similar compounds, may be found in U.S. Pat. No. 4,209,610, G.B. No. 1,543,081, European Patent Application No. 19,732 (published Dec. 10, 1980), U.S. Pat. No. 4,252,982 and commonly assigned copending application Ser. No. 355,812, now U.S. Pat. No. 4,395,466, filed of even date herewith. All of these are incorporated by reference herein.

As should be readily apparent, the compound of formula I will be produced as an isomeric mixture since the perfluorinated alcohol ($R_fOH$) can react with either carboxy group of each anhydride ring with respect to Q. Thus, for example, where the anhydride is a dianhydride, such as 3, 3', 4, 4'-benzophenone tetracarboxylic dianhydride (Q is —CO—), the product isolated is a mixture of three isomers which can be depicted by the formulae:

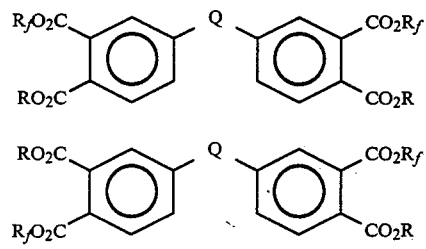

These isomers may also be depicted by the generic formula

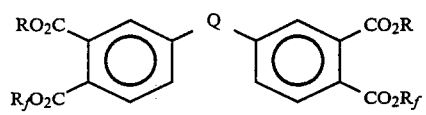

where the linking group Q is independently attached to the 4 or 5 position of each benzene ring with respect to the $CO_2R_f$ moiety.

An alternative synthetic route for preparing polyol esters falling within formula I, and other isomers thereof, may be utilized which is analagous to the route shown in U.S. Pat. Nos. 4,063,024 and 4,219,625 which are incorporated herein by reference. According to this technique a benzene tricarboxylic acid derivative, typically trimellitic anhydride acid chloride, is first condensed with the perfluorinated alcohol to form the monoester, which is then further condensed with the desired polyol $P(OH)_n$ to form the multi-ring perfluorinated polyol ester. The free carboxyl remaining on each ring may then be capped with a suitable R (epoxide) (or R-alcohol if the acid-chloride is formed). This reaction scheme may be depicted as follows:

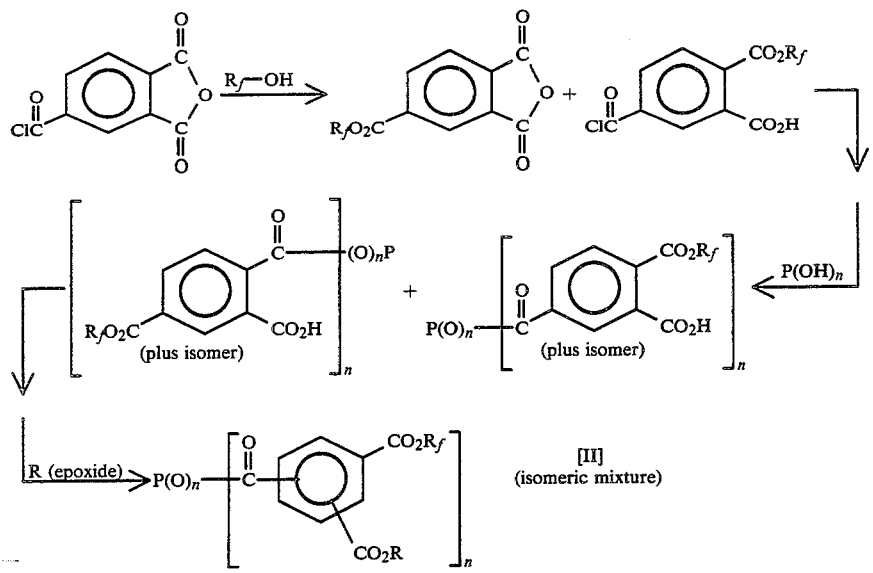

In the above reaction scheme, the polyol residue $P(O)_n$ may be derived from any organic polyol $P(OH)_n$ having 2 to 20 carbon atoms wherein n is as previously defined. It may be straight chain, branched chain, cyclic or aromatic in nature and may optionally contain hetero —O—, —S—, or —N atoms, as well as other substituents which are inert to esterification reactions. Preferably $P(O)_n$ is —$O(CH_2)_aO$—, —$(OCH_2CH_2)_bO$—, —$OCH(CH_2O)_2$, $CH_3C(CH_2O)_3$, $CH_3CH_2C(CH_2O)_3$, $C_4$, —$OC_6H_4O$— and $(CH_3)_2C(C_6H_4O)_2$ wherein a is 2 to 6 and b is 2 to 10.

As should be apparent, the above-described alternative route will produce a different isomeric mixture (formula II) than is obtained by utilizing the earlier described synthetic route (formula I).

The multi-ring anhydrides which are suitable for use in preparing compounds of the present invention following the first-described synthetic route are those having the formula

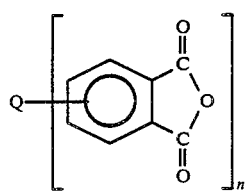

wherein Q and n are as previously defined.

Illustrative of these are:

Group I 3,3',4,4'-benzophenone tetracarboxylic dianhydride
2,3,3',4'-benzophenone tetracarboxylic dianhydride
2,2',3,3'-diphenyl tetracarboxylic dianhydride
3,3',4,4'-diphenyl tetracarboxylic dianhydride
2,2-bis(3,4-dicarboxyphenyl)propane dianhydride
2,2-bis(2,3-dicarboxyphenyl)propane dianhydride
1,1-bis(3,4-dicarboxyphenyl)ethane dianhydride
bis(2,3-dicarboxyphenyl)methane dianhydride
bis(3,4-dicarboxyphenyl)methane dianhydride
bis(3,4-dicarboxyphenyl)sulfone dianhydride
bis(3,4-dicarboxyphenyl)ether dianhydride
bis(3,4-dicarboxyphenyl)thioether dianhydride
bis(3,4-dicarboxyphenyl)amine dianhydride

Group II ethylene glycol di(trimellitate)dianhydride
polyethylene glycol di(trimellitate)dianhydride
glyceryl tri(trimellitate)trianhydride
pentaerythrityl tetra(triellitate)tetraanhydride
hydroquinone di(trimellitate)dianhydride The anhydrides of Group I are known in the art (see, for example, U.S. Pat. No. 3,959,229, G.B. No. 903,272, FR. No. 1,424,046) and may be prepared using conventional synthetic techniques (see, for example, U.S. Pat. No. 3,078,279, G.B. No. 1,477,519 and Lavrova et al, *Volokna Sin. Polim.* 1970, 15–24 (Chem. Abs. 76:33912W)). Of these, 3,3',4,4'-benzophenone tetracarboxylic dianhydride ("BTDA") is preferred because of its commercial availability.

The anhydrides of Group II are readily synthesized by selective high temperature esterification of trimellitic acid anhydride (or monoacid chloride) with the desired polyol. The reaction scheme may be depicted as follows.

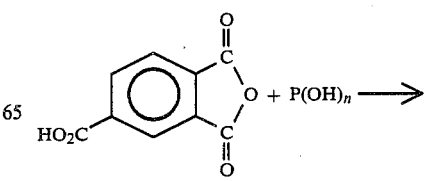

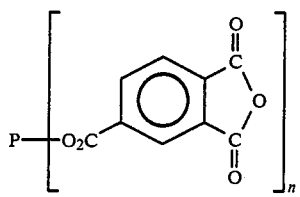

wherein P represents the polyol residue.

The fluorinated radicals $R_f$ which may be present in the compounds of this invention are derived from the corresponding fluorinated alcohols ($R_f$—OH) which are known in the art and described in U.S. Pat. Nos. 3,171,861, 3,514,487, 3,646,153, 3,697,564, 4,209,610 and 4,219,681, all of which are incorporated herein by reference.

Typical of these are fluorinated alcohols of the formula HO—W($C_dF_{2d}$)Y wherein W has from 1 to 10 carbon atoms and is selected from alkylene and W'—Z—(W")$_e$ where W' and W" are alkylene, Z is O, S, NHCO, or $NHSO_2$, and e is 0 or 1, Y is hydrogen, fluoro, or perfluoroalkoxy of 1 to 6 carbon atoms, and d is 2 to 20. The preferred fluorinated alcohols, because of their commercial availability, are the perfluoroalkylethanols and omega-perfluoroisopropoxyperfluoroalkyl ethanols having two to twelve carbon atoms in the perfluoroalkyl groups, as well as the propanol homologues thereof. Most preferred are the perfluoroalkyl ethanols having six to twelve carbon atoms in the perfluoroalkyl groups, and mixtures thereof.

The soil-repellent compounds of the present invention may be incorporated into polyester or nylon fibers using several known methods. In one method the compound is blended with the resin prior to being extruded into fibers. In another method, the compound may be applied to the fiber by absorption from a liquid medium, for example as a solution in an organic solvent or as an emulsion or dispersion in aqueous medium. In either method the fibers are generally annealed at elevated temperatures after treatment. Typically the compounds are incorporated in the fibers in an amount of from about 0.1 to 1% by weight and the treated fibers are annealed at temperatures of about 100° to 220° C. for about 1 to 240 minutes to impart the desired soil repellency. Further details of the above methods are disclosed in U.S. Pat. Nos. 4,209,610 and 4,219,625 which are incorporated herein by reference.

The invention may be described in greater detail by the following examples in which the parts and percentages are by weight. In each of the examples the fluorinated alcohol employed is a mixture of perfluoroalkyl ethanols having six to twelve carbon atoms in the perfluoroalkyl group. The structure of each product prepared is shown in Table 1 following the examples.

EXAMPLE 1

Into a reaction flask were added 38.8 g 3,3',4,4'-benzophenone tetracarboxylic acid dianhydride (Gulf BTDA, 98.5%, 237 meq), 108 g perfluoroalkyl ethanol (237 meq), 86 g N-methylpyrrolidone (NMP) and 0.95 ml triethylamine. This mixture was stirred at 55° C. for 9.5 hours and then 55.8 ml epichlorohydrin were added. This mixture was stirred at 55° C. for 15 hours and the product isolated by drowning into water, washing with water to remove solvent and excess epoxide (epichlorohydrin), and drying under vacuum (yield 97.7 g).

EXAMPLE 2

Into a reaction flask were added 19.4 g BTDA (120 meq), 54 g NMP, 54 g perfluoralkyl ethanol (118 meq) and 0.5 ml triethylamine. This mixture was stirred for 7 hours at 55° C., at which point GC analysis indicated most of the alcohol had been consumed. A total of 11.8 g ethylene oxide was added to the mixture over 6 hours at 40° C., followed by heating at 50° C. for an additional 5.5 hours. At this point another 9.0 g ethylene oxide was added at 50° C. and the stirring continued for another 12 hours. Titration for carboxyl group indicated the reaction to be essentially complete at this point and the product was isolated as in Example 1 (yield 23.2 g).

EXAMPLE 3

Into a reaction flask were added 65 g NMP, 33.8 g perfluoroalkyl ethanol (73.6 meq), 20 g of ethylene glycol di(trimellitate)dianhydride (73.4 meq; Additol VXL 1524 from Hoechst AG), and 0.95 ml triethylamine. This mixture was stirred at 55° C. for 4 hours, then 17.1 ml epichlorohydrin (220 meq) was added. This mixture was stirred at 55° C. until carboxyl titration indicated the reaction to be essentially complete (about 28 hours), and the product isolated as in Example 1 (yield 24.4 g).

EXAMPLE 4

Into a reaction flask were added 135 g NMP, 84.7 g perfluoroalkyl ethanol (184 meq), 80 g polyethylene glycol (200) di(trimellitate)dianhydride (184 meq, condensation product of PEG 200 and trimellitic anhydride acid chloride), and 1.93 ml triethylamine. The mixture was stirred for 4 hours at 60° C., after which time GC analysis indicated the presence of unreacted alcohol. An additional 8 g of anhydride was added and the mixture stirred for 1 hour at room temperature. GC showed about 2% residual alcohol. At this point 55.8 g epichlorohydrin was added and the reaction mixture stirred for 13 hours at 75° C., when carboxyl titration indicated the reaction to be complete. The product was isolated as in Example 1 (yield 76 g).

EXAMPLE 5

Into a reaction flask were added 20 g of ethylene glycol di(trimellitate)dianhydride (73.4 meq, Additol VXL 1524), 65 g NMP, 33.67 g perfluoroalkyl ethanol (73.4 meq) and 0.95 ml triethylamine. After stirring this mixture at 55° C. for 4 hours, 14.1 g ethylene oxide was added subsurface over 3.5 hours at 45° C., followed by stirring overnight at room temperature. The reaction mixture was then heated to 45° C. and 4.3 g ethylene oxide were added over 1 hour. This mixture was stirred 5 hours at 55° C., 1.6 g ethylene oxide added, and the stirring continued for 18 hours at which time titration for residual carboxyl groups indicated the reaction to be essentially complete. The product was isolated as in Example 1 (yield 16.4 g).

EXAMPLE 6

Into a reaction flask were added 30 g glyceryl tri(trimellitate)trianhydride (130.8 meq, condensation product (tri-ester) of glycerol and trimellitic anhydride acid chloride), 124.2 g NMP, 65.7 g perfluoroalkyl ethanol (130.8 meq) and 1.49 ml triethylamine. After stirring this mixture for 5 hours at 55° C., 36.3 g epichlorohydrin (392.4 meq) was added and the reaction mixture stirred at 65° C. for 13.5 hours when carboxyl titration indicated the reaction to be essentially complete. The product was isolated as in Example 1 (yield 60.7 g).

EXAMPLE 7

Into a reaction flask were added 21.7 g of 97% trimellitic anhydride acid chloride (100 meq) and 48 g NMP. After stirring the mixture for 10 minutes, 45.8 g (100 meq) perfluoroalkyl ethanol was added over about one hour and the reaction temperature climbed to about 45° C. The reaction was held at 40° C. for 1.5 hours and the temperature then raised to 80° C. and held for another 2.5 hours. G.C. analysis at this point indicated that all of the alcohol had been consumed. After cooling the mixture to room temperature, 3.1 g ethylene glycol (50 meq) and 0.5 ml triethylamine were added and the temperature raised to 55° C. and held for six hours. At this point 27.7 g epichlorohydrin (300 meq) was added and the mixture stirred at 55°–60° C. for 23 hours, at which time carboxyl titration indicated that the reaction was essentially complete. The product was isolated as in Example 1 (yield 63 g).

The compounds prepared in the above examples may be depicted by the structural formulae shown in Table I, wherein Q, n, P(O)$_n$, R and R$_f$ are as defined therein.

according to AATCC Test 118-1975, the rating scale running from 0-8 with increasing numbers indicating greater repellency. Each fabric was also tested before washing as well as after the wash tests. For long term washfastness the more rigorous IIIA Test was carried out repeatedly, each repeat simulating five home launderings at high temperature. The results of the testing for oil repellency are shown in Table II.

TABLE II

| Example | Fabric | OIL REPELLENCY | | | | | |
|---|---|---|---|---|---|---|---|
| | | Before Washing | After IIA Wash | After IIIA Wash | | | |
| | | | | 1× | 2× | 3× | 4× |
| 1 | Nylon | 6 | 6 | 6 | 6 | 6 | 6 |
| | Poly | 6 | 6 | 6 | 6 | 6 | 6 |
| 2 | Poly | 6 | 5 | — | — | — | — |
| 3 | Nylon | 6 | 6 | 6 | 6 | 1 | 0 |
| | Poly | 5 | 5 | 5 | 5 | 5 | 2 |
| 4 | Nylon | 6 | 5 | 5 | 0 | 2 | 0 |
| | Poly | 6 | 5 | 5 | 5 | 5 | 4 |
| 5 | Nylon | 6 | 0 | — | — | — | — |
| | Poly | 5 | 4 | — | — | — | — |
| 6 | Nylon | 6 | 5 | 3 | 2 | 0 | 0 |
| | Poly | 6 | 5 | 5 | 5 | 5 | 4 |
| 7 | Nylon | 6 | 6 | — | — | — | — |
| | Poly | 5 | 2 | — | — | — | — |

TABLE I

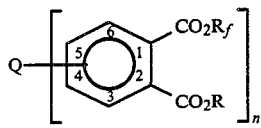

R$_f$ is —CH$_2$CH$_2$(CF$_2$CF$_2$)$_j$CF$_2$CF$_3$ where j is 2 to 5 (mixture).
Q is at 4 or 5 position with respect to CO$_2$R$_f$ (isomeric mixture).

Ex. 1  Q = $\overset{O}{\underset{\|}{-C-}}$  n = 2  R = —CH$_2$CH(OH)CH$_2$Cl

Ex. 2  Q = $\overset{O}{\underset{\|}{-C-}}$  n = 2  R = —CH$_2$CH$_2$OH

Ex. 3  Q = —CO$_2$CH$_2$CH$_2$O$_2$C—  n = 2  R = —CH$_2$CH(OH)CH$_2$Cl
Ex. 4  Q = —CO(OCH$_2$CH$_2$)$_{2-6}$O$_2$C—  n = 2  R = —CH$_2$CH(OH)CH$_2$Cl
Ex. 5  Q = —CO$_2$CH$_2$CH$_2$O$_2$C—  n = 2  R = —CH$_2$CH$_2$OH
Ex. 6  Q = —CO$_2$CH(CH$_2$O$_2$C)$_2$  n = 3  R = —CH$_2$CH(OH)CH$_2$Cl

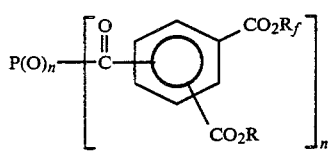

Ex. 7  P(O)$_n$ = —OCH$_2$CH$_2$O—  n = 2  R = —CH$_2$CH(OH)CH$_2$Cl

Application of Compounds to Fiber

Each of the compounds prepared in Examples 1 to 7 was applied to fiber by dissolving the compound in acetone and applying it to nylon and/or polyester fabric through a padder. The concentration of compound in solution was adjusted so that pick up was 0.25% compound compared to the weight of the fabric. After drying at room temperature, the fabric was cured (annealed) at 140° C. (nylon) or 160° C. (polyester) for 30 minutes.

The treated fabrics were then subjected to AATCC Test 61-1968 Wash IIA or IIIA using a launderometer from Atlas Electric Company to simulate five home launderings at medium or high temperature settings. The washed fabric was evaluated for oil repellency

What is claimed is:
1. A compound of the formula

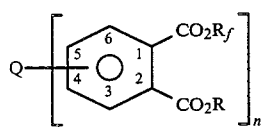

wherein
n is 2 or 3;

Q has a valence equal to n and is selected from the group consisting of, $(C_aH_{2a+2-\overline{n}})(O_2C)_{\overline{n}}$, $-CO(OCH_2CH_2)_bO_2C-$, $-CO_2C_6H_4O_2C-$, and $(CH_3)_2C(C_6H_4O_2C)_{\overline{2}}$, wherein a is 2 to 6, b is 2 to 10, and n is as defined above but cannot exceed a;

R is selected from $-CH_2CH(R_1)OH$, $-CH_2CH(R_1)OCH_2CH(R_1)OH$, $-CH_2CH(OH)CH_2X$, or $-CH_2CH(OH)CH_2OCH_2CH(OH)CH_2X$ wherein $R_1$ is hydrogen or methyl and X is chloro, bromo, hydroxy, or cyano; and $R_f$ is a fluorinated radical of the formula $-W(C_dF_{2d})Y$ wherein W has from 1 to 10 carbon atoms and is selected from alkylene and $W'-Z-(W'')_e$ where $W'$ and $W''$ are alkylene, Z is O, S, NHCO, or NHSO$_2$, and e is 0 or 1, Y is hydrogen, fluoro, or perfluoroalkoxy of 1 to 6 carbon atoms, and d is 2 to 20.

2. A compound according to claim 1 wherein Q is selected from $-CO_2(CH_2)_aO_2C-$, $-CO(OCH_2CH_2)_bO_2C-$, $-CO_2CH(CH_2O_2C)_2$, $CH_3C(CH_2O_2C)_3$, $CH_3CH_2C(CH_2O_2C)_3$, $C_4$, $-CO_2C_6H_4O_2C-$, and $(CH_3)_2C(C_6H_4O_2C)_2$.

3. A compound according to claim 2 wherein Q is independently located at the 4 or 5 position of each benzene ring with respect to the $-CO_2R_f$ moiety.

4. A compound according to claim 3 wherein W is alkylene of 2 to 6 carbon atoms, d is 2 to 12, and R is $-CH_2CH_2OH$, $-CH_2CH(OH)CH_2Cl$, $-CH_2CH(OH)CH_2OH$, or $-CH_2CH(OH)CH_2Br$.

5. A compound according to claim 4 wherein $R_f$ is selected from $-CH_2CH_2(CF_2)_gCF_3$ or $-CH_2CH_2(CF_2)_hOCF(CF_3)_2$ wherein g is 5 to 11 and h is 2 to 12.

6. A compound according to claim 5 wherein $R_f$ is $-CH_2CH_2(CF_2CF_2)_jCF_2CF_3$ and j is 2 to 5.

7. A compound according to claim 6 wherein R is $-CH_2CH_2OH$ or $-CH_2CH(OH)CH_2Cl$.

8. A compound according to claim 5 having the formula

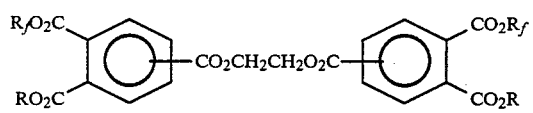

9. A compound according to claim 5 having the formula

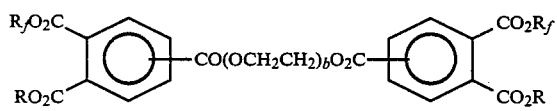

wherein b is 2 to 6.

10. A compound according to claim 5 having the formula

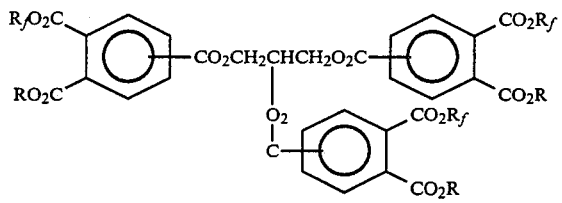

11. A compound of the formula

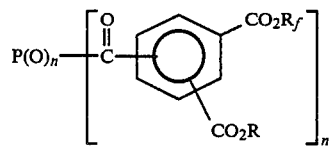

wherein
n is 2 or 3;

$P(O)_n$ is the residue of an organic polyol $P(OH)_n$ having 2-20 carbon atoms wherein n is as defined above;

R is selected from $-CH_2CH(R_1)OH$, $-CH_2CH(R_1)OCH_2CH(R_1)OH$, $-CH_2CH(OH)CH_2X$, or $-CH_2CH(OH)CH_2OCH_2CH(OH)CH_2$ wherein $R_1$ is hydrogen or methyl and X is chloro, bromo, hydroxy, or cyano; and $R_f$ is a fluorinated radical of the formula $-W(C_dF_{2d})Y$ wherein W has from 1 to 10 carbon atoms and is selected from alkylene and $W'-Z-(W'')_e$ where $W'$ and $W''$ are alkylene, Z is O, S, NHCO, or NHSO$_2$, and e is 0 or 1, Y is hydrogen, fluoro, or perfluoroalkoxy of 1 to 6 carbon atoms, and d is 2 to 20.

12. A compound of claim 11 wherein $P(O)_n$ is selected from $-O(CH_2)_aO-$, $-(OCH_2CH_2)_bO-$, $-OCH(CH_2O)_{\overline{2}}$, $CH_3C(CH_2O)_{\overline{3}}$, $CH_3CH_2C(CH_2O)_{\overline{3}}$, $-OC_6H_4O-$ and $(CH_3)_2C(C_6H_4O)_2$ wherein a is 2 to 6 and b is 2 to 10.

13. A compound according to claim 12 wherein W is alkylene of 2 to 12 carbon atoms, d is 2 to 12, and R is $-CH_2CH_2OH$, $-CH_2CH(OH)CH_2Cl$, $-CH_2CH(OH)CH_2OH$, or $-CH_2CH(OH)CH_2Br$.

14. A compound according to claim 13 wherein $R_f$ is selected from $-CH_2CH_2(CF_2)_gCF_3$ or $-CH_2CH_2(CF_2)_hOCF(CF_3)_2$ wherein g is 5 to 11 and h is 2 to 12.

15. A polyester or polyamide fiber having incorporated therewith a compound of claim 1 or 11 in an amount sufficient to impart oil or water repellency.

16. A process of incorporating a compound of claim 1 into the surface of a polyester or polyamide fiber which comprises contacting said compound in liquid medium with said fiber and thereafter annealing the resulting fiber at elevated temperature, the amount of said compound and the time and temperature of annealing being sufficient to impart oil or water repellency to said fiber.

* * * * *

UNITED STATES PATENT AND TRADEMARK OFFICE
CERTIFICATE OF CORRECTION

PATENT NO. : 4,595,628
DATED : June 17, 1986
INVENTOR(S) : Kelly et al

It is certified that error appears in the above-identified patent and that said Letters Patent is hereby corrected as shown below:

IN THE SPECIFICATION:

At column 4, line 22, after the formula "$CH_3CH_2C(CH_2O_2C)_{\overline{3}}$" delete the term "$C_4$"

At column 7, line 40, at the beginning of the line delete the term "$C_4$".

IN THE CLAIMS:

In Claim 2, column 13, line 22, the formula "$-CO_2CH(CH_2O_2C)2$" should read "$-CO_2CH(CH_2O_2C)_{\overline{2}}$".

In Claim 2, column 13, line 23 after the formula "$CH_3CH_2C(CH_2O_2C)_3$" delete the term "$C_4$".

Signed and Sealed this

Twenty-eighth Day of October, 1986

[SEAL]

*Attest:*

DONALD J. QUIGG

*Attesting Officer*  *Commissioner of Patents and Trademarks*